United States Patent [19]

Masini et al.

[11] Patent Number: 4,985,214
[45] Date of Patent: Jan. 15, 1991

[54] SIMULTANEOUS PRODUCTING OF HIGHER CHLOROMETHANES

[75] Inventors: Jean-Jacques Masini, Chaponost; Yvan Verot, Ecully, both of France

[73] Assignee: Atochem, Puteaux, France

[21] Appl. No.: 189,832

[22] Filed: May 3, 1988

Related U.S. Application Data

[60] Division of Ser. No. 99,783, Sep. 22, 1987, Pat. No. 4,765,876, which is a continuation of Ser. No. 773,927, Sep. 9, 1985, abandoned, which is a continuation of Ser. No. 619,357, Jun. 11, 1984, abandoned.

[30] Foreign Application Priority Data

Jun. 10, 1983 [FR] France ............................. 83 09667

[51] Int. Cl.$^5$ ............................................. B01J 19/00
[52] U.S. Cl. ................................... 422/188; 422/189; 422/234; 570/255
[58] Field of Search ................ 570/255; 422/188, 189, 422/234

[56] References Cited

U.S. PATENT DOCUMENTS 3,126,419 3/1964 Burks, Jr. et al. ................... 570/255
3,848,007 11/1974 Forlano ............................... 570/255
4,456,778 6/1984 Zölffel et al. ....................... 570/255

Primary Examiner—Robert J. Warden
Assistant Examiner—Timothy M. Mahon
Attorney, Agent, or Firm—Burns, Doane, Swecker & Mathis

[57] ABSTRACT

Apparatus for the production of higher chloromethanes, i.e, $CH_2Cl_2$, $CHCl_3$ and $CCl_4$, by chlorinating methyl chloride with chlorine in a first reaction zone A, chlorinating at least one of the higher chloromethanes $CH_2Cl_2$ and $CHCl_3$ with chlorine in a parallel second reaction zone B, combining the reaction products from the first and second reaction zones A and B, separating higher chloromethanes from the combined reaction prodcuts, and recycling at least one of the separated higher chloromethanes $CH_2Cl_2$ and $CHCl_3$ as chlorination feed to the second reaction zone B.

23 Claims, 1 Drawing Sheet

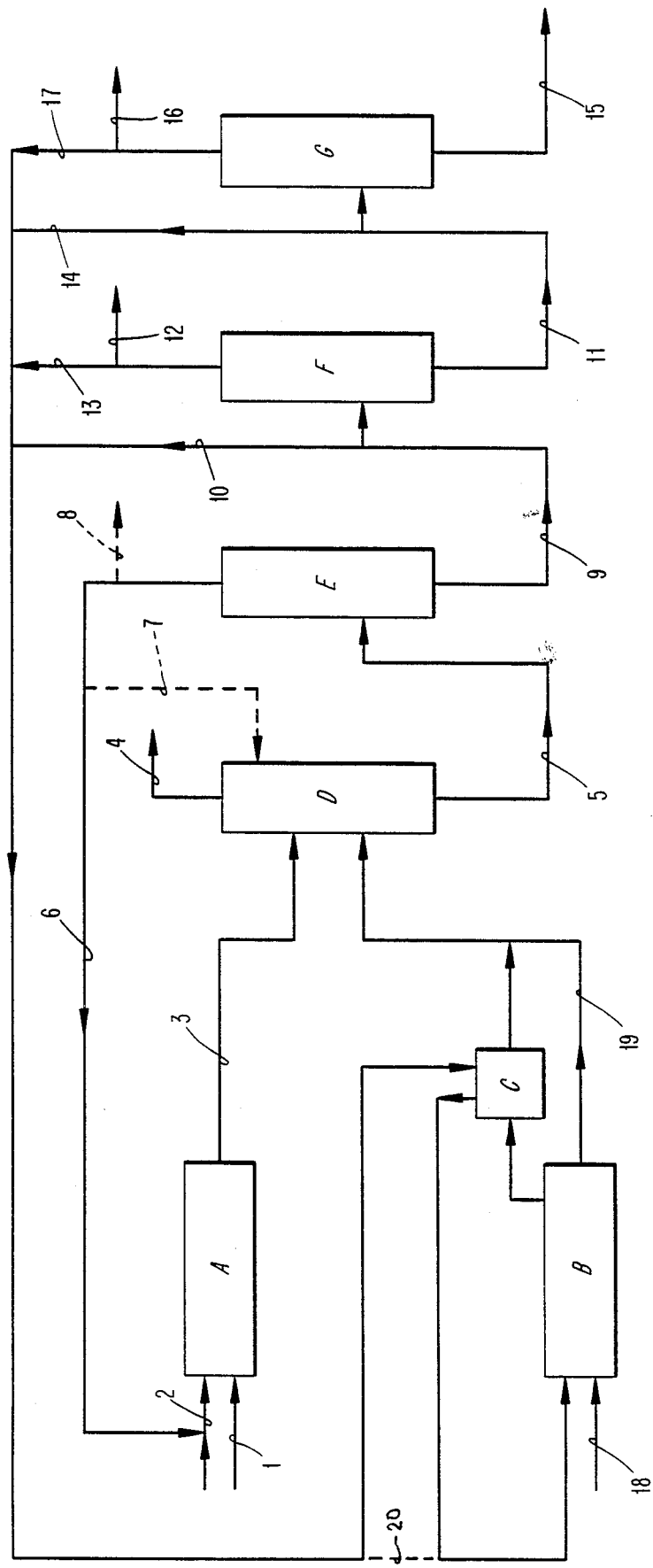

4,985,214

SIMULTANEOUS PRODUCTING OF HIGHER CHLOROMETHANES

This application is a divisional of application Ser. No. 099,783 filed Sept. 22, 1987 and now U.S. Pat. No. 4,765,876, which is a continuation of Ser. No. 773,927 filed Sept. 9, 1985, abandoned, which is a continuation of Ser. No. 619,357 filed June 11, 1984, abandoned.

BACKGROUND OF THE INVENTION

1. Field of the Invention

The present invention relates to the preparation of higher chloromethanes by chlorination of methyl chloride, and, more especially, to the simultaneous such preparation of select amounts of the three higher chloromethanes $CH_2Cl_2$, $CHCl_3$ and $CCl_4$.

2. Description of the Prior Art

Conventional processes for the preparation of higher chloromethanes by chlorination of $CH_3Cl$, as a practical matter, result only in the production of $CH_2Cl_2$ and $CHCl_3$. The $CCl_4$ coproduct constitutes less than 15% of the total production and is thus considered to be only a by-product of the reaction.

The production of $CCl_4$ is typically carried out by so-called "Tetra-per" (carbon tetrachloride/perchloroethylene) processes from chlorinated residues and/or saturated or olefinic hydrocarbons having two or three carbon atoms. However, such techniques lead to the generation of a not inconsiderable amount of heavy by-products. In addition, they consume large amounts of energy.

Because of these disadvantages of conventional processes, the preparation of $CCl_4$ from chloromethanes originating from the chlorination of $CH_3Cl$ would be of interest, especially since the most recent improvements in this process permit free radical chlorination in the liquid phase at a low temperature, using a chemical or photochemical initiator. Such processes are economical due to the high yields obtained and the simplification of the separation operations, the amount of troublesome by-products produced being small.

However, in the current state of the art, the simultaneous production of prescribed amounts, which may be close to one another, of the three higher chloromethanes does not proceed without giving rise to problems in the conventional apparatus which consists of a reactor for the chlorination of $CH_3Cl$ followed by downstream columns for purifying and separating the various products of reaction. Such a system lacks flexibility. In fact, in this type of unit, the principal constraint is the adjustment for the respective productions of produced is a $CH_2Cl_2$ and $CHCl_3$; $CHCl_4$ simultaneously function of the $CH_2Cl_2$—$CHCl_3$ proportion effectively obtained and the operating conditions. This production of $CCl_4$ can only be low with respect to that of the other two chloromethanes.

The production of prescribed amounts, which may be close to one another, of the three higher chloromethanes in conventional apparatus comprising a single chlorination reactor must necessarily be balanced by the total amount of invenstment required for profitable operation. In fact, in this type of unit, the adjustment in the flexibility is obtained by limiting the degree of conversion of $CH_3Cl$ and, if necessary, by appropriate recycling of $CH_2Cl_2$. This manifests itself in a significant over-dimensioning in the entirety of the apparatus concerned, and concomitant marked increase in operating costs. Moreover, the productivity of a given reactor, all things otherwise being equal, is sensitive to the composition of the higher chloromethanes produced. It is known that the rate of chlorination of a chloromethane substantially decreases as the number of chlorine atoms contained in the molecule increases: a reactor having a productivity of 100 for respective compositions of $CH_2Cl_2$, $CHCl_3$ and $CCl_4$ of about 45/45/10% by weight would only have, all things otherwise again being equal, a productivity of about 65 for a distribution of 37.5/47.5/15 and of 30 for 20/45/35. "Productivity" is defined as the amount of chlorine reacted per unit volume of the reactor for a fixed level of unreacted chlorine at the outlet of the reactor.

SUMMARY OF THE INVENTION

Accordingly, a major object of the present invention is the provision of improved chlorination apparatus/process, said apparatus comprising two reactors A and B in parallel, with reactor A operating in conventional manner for the chlorination of methyl chloride and reactor B, which is fed with chlorine and $CH_2Cl_2$ and/or $CHCl_3$ produced in reactor A, serving to produce either the higher chloromethanes $CHCl_3$ and $CCl_4$ simultaneously, or $CCl_4$ by itself, and to ensure high flexibility respecting the overall apparatus.

Briefly, in the subject process adjustment in the production of $CH_2Cl_2$, $CHCl_3$ and $CCl_4$ is effected by adapting, on the one hand, the distribution and amount of products formed in reactor A and, on the other hand, the production and the ratio of the amounts of $CH_2Cl_2$ and $CHCl_3$ converted in reactor B.

BRIEF DESCRIPTION OF THE DRAWING

The FIGURE of drawing is a schematic/diagrammatic illustration of apparatus suitable for carrying out the process according to the invention.

DETAILED DESCRIPTION OF THE INVENTION

More particularly according to the present invention, with reference to the accompanying FIGURE of drawing, the reactor A is fed with $Cl_2$ and $CH_3Cl$, respectively, via the lines 1 and 2. The reaction products are transferred via line 3 into a separation unit D: $HCl/CH_3Cl$/higher chloromethanes, with HCl being removed via line 4 and $CH_3Cl$ and the higher chloromethanes being conveyed via line 5 into the separation unit E. Unreacted $CH_3Cl$ is removed via line 8 or recycled via line 6 to reactor A. In order to limit the temperature at the base of the tank of unit D, it is also possible to recycle more or less $CH_3Cl$ via line 7. The higher chloromethanes are conveyed via line 9 into the separation unit F for separating $CH_2Cl_2$ from the other higher chloromethanes, it being possible for all or some of the $CH_2Cl_2$ to be recovered at 12 or for all or some of it to be recycled via line 13 into reactor B. Finally, the remaining higher chloromethanes are conveyed via line 11 into the separation unit G for separating $CHCl_3$ from crude $CCl_4$, it being possible for all or some of the $CHCl_3$ to be recovered at 16 or for all or some of it to be recycled via line 17 into reactor B, the crude $CCl_4$ being recovered at 15. Provision may be made for recycling the higher chloromethanes into reactor B via lines 10 and 14. In this case, $CCl_4$, which does not interfere with the reaction products, is recycled into reactor B. This $CCl_4$ thus plays the role of diluent for the reactants and in this manner may decelerate the reaction; as a result, this recirculation should preferably be limited.

Before the higher chloromethanes are introduced into reactor B, it may be useful to first circulate them into a gas-scrubbing device C which enables the gaseous phase issuing from reactor B to be scrubbed. In the case where the gas scrubbing device C is omitted, the higher chloromethanes can be fed to reactor B by means of line 20.

The higher chloromethanes react, in reactor B, with $Cl_2$ introduced via line 18. The reaction products are combined via line 19 with those of reactor A in the simplest manner, in the separation unit D.

It is recommended, although this is not essential, that the chloromethanes being charged to reactor B contain as little $CH_3Cl$ as possible, such that this reactor at the same time maintains an acceptable selectivity and productivity for the given degrees of conversion of $CH_2Cl_2$ and/or $CHCl_3$.

The adjustment in the amounts of $CH_2Cl_2$ converted and $CHCl_3$ converted or produced is effected by adaptation of the composition of $CH_2Cl_2$ and $CHCl_3$ in the reactor, as well as the rate at which the reactor is fed. The reaction parameters of each of the reactors, and of course the reactors themselves, are adapted such that the reactions take place in the liquid phase. The pressures in each reactor are in general close to one another and should be selected such that the separation of HCl and the chloromethanes is facilitated. Good results are obtained using temperatures in the reactors ranging from 50° to 120° C., preferably from 60° to 90° C., under pressures of 10 to 50 bar, preferably 15 to 25 bar. The ratio in reactor A between the number of molecules of $Cl_2$ and the number of molecules of $CH_3Cl$ advantageously ranges from 0.3:1 to 1.5:1, preferably from 0.5:1 and 1:1. The amount of $Cl_2$ introduced into reactor B is selected as a function of the amount of each of the higher chloromethanes introduced and of the higher chloromethane or chloromethanes desired to be ultimately obtained. The chlorination reactions in the reactors A and B are known per se, and are usually reactions of the free radical type, with initiation thereof being by means of a chemical or photochemical initiator.

The reaction products exit the reactors A and B in liquid or gaseous form. It is possible, although this is not essential, to scrub the gaseous phases with higher chloromethane in order to recover the trace amounts of chlorine which are contained therein and which constitute most of the unreacted chlorine. This scrubbing is of particular interest with respect to the products of reactor B. Such a scrubbing enables the excess chlorine to be recovered and as a result thereof significantly increases the productivity of the reactor.

The various reaction products of the reactors A and B are separated from each other in the downstream separation units, described above, under the typical distillation conditions appropriate for each of such products.

The process according to the invention has the advantage of concentrating the problems of limitation in productivity in a single auxiliary reactor B, which very substantially obviates same by reason of the fact that the reaction material in this reactor is formed from $CH_2Cl_2$ and/or $CHCl_3$. Another advantage concerns the flexibility, which is particularly significant in the reaction unit and which preserves, in addition, all the economic advantages of the conventional process. In fact, for a given production of $CCl_4$, which may be up to 50% of the total production, the $CH_2Cl_2$—$CHCl_3$ distribution in the complement of the production may vary continuously over wide ranges, and more particularly, from an economic point of view, between 75/25 and 25/75% by weight.

In order to further illustrate the present invention and the advantages thereof, the following specific examples are given, it being understood that same are intended only as illustrative and in nowise limitative.

EXAMPLE 1

A reactor A was continuously charged with 0.15 kmoles/hour of liquid chlorine and 0.185 kmoles/hour of liquid $CH_3Cl$. This reactor was a perfectly stirred photochemical reactor operating under a pressure of 15 bar absolute and at 60° C. and cooled by water circulation; the reaction products had the following approximate composition (mixture of liquid+vapor):

|  | % by weight |
|---|---|
| HCl = | 27.2 |
| $CH_3Cl$ = | 22.7 |
| $Cl_2$ | <0.5% of the mixture of the other compounds |
| $CH_2Cl_2$ = | 22.1 |
| $CHCl_3$ = | 22 |
| $CCl_4$ = | 6 |

A reactor B was continuously charged with 0.021 kmoles/hour of liquid chlorine and 0.043 kmoles/hour of liquid $CHCl_3$. This reactor was identical to the reactor A and operated under the same operating parameters. The reaction products therefrom had the following approximate composition (mixture of liquid+vapor):

|  | % by weight |
|---|---|
| HCl = | 11.8 |
| $Cl_2$ | <1% of the mixture of HCL + $CHCl_3$ + $CCl_4$ |
| $CHCl_3$ = | 38.5 |
| $CCl_4$ = | 49.7 |

The two reaction mixtures were transferred into a distillation column operating under a pressure of 12 bar absolute, in which the HCl was separated from the other reaction products. A product having the following approximate composition was drawn off:

|  | % by weight |
|---|---|
| $CH_3Cl$ = | 22.2 |
| $CH_2Cl_2$ = | 21.7 |
| $CHCl_3$ = | 34.1 |
| $CCl_4$ = | 22 |

This mixture thus obtained was then separated by successive distillation such that each of the chloromethanes was obtained, i.e., the equivalent of:

|  | kmoles/hour |
|---|---|
| $CH_3Cl$ = | 0.089 |
| $CH_2Cl_2$ = | 0.051 |
| $CHCl_3$ = | 0.058 |
| $CCl_4$ = | 0.029 | was thus obtained.

Thus, taking into account the recycling of 0.043 kmoles/hour of $CHCl_3$ into the reactor B, the production of higher chloromethanes was hence approximately:

|  | kmoles/hour |
|---|---|
| $CH_2Cl_2 =$ | 0.051 |
| $CHCl_3 =$ | 0.015 |
| $CCl_4 =$ | 0.029 | which gave an amount, by weight of $CH_2Cl_2$ and $CHCl_3$ in the $CH_2Cl_2+CHCl_3$ mixture, of, respectively, 70.3% and 29.7%.

EXAMPLE 2

The experiment of Example 1 was repeated, but an amount of $CCl_4$ corresponding to about 20% by weight of the chloroform was added to the chloroform charged to the reactor B. The only noticeable change in respect of the results obtained in Example 1 was the increase in unreacted chlorine in the reactor B.

EXAMPLE 3

Reactor A was operated under the same conditions as described in Example 1.

Reactor B was in this Example charged with 0.029 kmole/hour of liquid $CH_2Cl_2$ and 0.05 kmole/hour of liquid chlorine. It operated under the same operating conditions as in Example 1. The reaction products had the following approximate composition (mixture of liquid + vapor):

|  | % by weight |
|---|---|
| $HCl =$ | 30 |
| $Cl_2$ | <95 of the total mixture |
| $CH_2Cl_2 =$ | 2 |
| $CHCl_3 =$ | 14 |
| $CCl_4 =$ | 54 |

After separation of the reaction products, the equivalent of:

|  | kmoles/hour |
|---|---|
| $CH_2Cl_2 =$ | 0.053 |
| $CHCl_3 =$ | 0.043 |
| $CCl_4 =$ | 0.029 | was thus collected.

Taking into account the recycling of 0.029 kmole/hour of $CH_2Cl_2$ to the reactor B, the production of higher chloromethanes was thus approximately:

|  | kmoles/hour |
|---|---|
| $CH_2Cl_2 =$ | 0.024 |
| $CHCl_3 =$ | 0.043 |
| $CCl_4 =$ | 0.029 | which gave an amount, by weight of $CH_2Cl_2$ and $CHCl_3$ in the $CH_2Cl_2 + CHCl_3$ mixture, of, respectively, 27.8% and 72.2%.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What is claimed is:

1. Apparatus for the simultaneous preparation of the higher chloromethanes $CH_2Cl_2$, $CHCl_3$ and $CCl_4$, comprising parallel first and second chlorination reaction means A and B, means for reaction product combination and separation in downstream, discrete communicating relationship with each of said reaction means A and B, means for separating higher chloromethanes from combined reaction product, and means for recycling at least one separated higher chloromethane directly from said separating means to said second reaction means B.

2. The apparatus as defined by claim 1, wherein said means for separation of the reaction product comprises a plurality of downstream means for separation of said combined reaction product, in serially communicating relationship.

3. The apparatus as defined by claim 2, further comprising means for gas scrubbing feed to said second reaction means B.

4. The apparatus as defined by claim 3, wherein said first reaction means A includes means for feeding methyl chloride thereto and said second reaction means B includes means for feeding at least one higher chloromethane thereto, said separation means comprising a first separation unit for removing HCl from the reaction product, a second separation unit for removing $CH_3Cl$ from the reaction product, a third separation unit for removing $CH_2Cl_2$ from the reaction product and a fourth separation unit for removing $CHCl_3$ from the reaction product.

5. The apparatus as defined by claim 4, wherein said second separation unit is located downstream of said first separation unit, said third separation unit is located downstream of said second separation unit and said fourth separation unit is located downstream of said third separation unit.

6. The apparatus as defined by claim 4, further comprising means for feeding unreacted $CH_3Cl$ removed by said second separation unit to feed to said first reaction means A.

7. The apparatus as defined by claim 4, further comprising means for feeding reaction product exiting said second separation unit to feed to said second reaction means B.

8. The apparatus as defined by claim 4, further comprising means for feeding reaction product exiting said third separation unit to feed to said second reaction means B.

9. Apparatus for the simultaneous preparation of the higher chloromethanes $CH_2Cl_2$, $CHCl_3$ and $CCl_4$, comprising parallel first and second chlorination reaction means A and B, means for reaction product combination and separation in downstream, discrete communicating relationship with each of said reaction means A and B, means for separating higher chloromethanes from combined reaction product, and means for recycling at least one separated higher chloromethane to said second reaction means B, the apparatus further comprising means for scrubbing effluent from said second reaction means B located upstream of said means for reaction product combination.

10. Apparatus for the simultaneous preparation of the higher chloromethanes $CH_2Cl_2$, $CHCl_3$ and $CCl_4$, comprising parallel first and second chlorination reaction means A and B, means for reaction product combination and separation in downstream, discrete communicating relationship with each of said reaction means A and B, means for separating higher chloromethanes from combined reaction product, and means for recycling at least one separated higher chloromethane to said second reaction means B, the apparatus further comprising means for scrubbing effluent from said second reaction means B located upstream of said means for reaction product combination, said scrubbing means including means for gas scrubbing feed to said second reaction means B.

11. Apparatus for the simultaneous preparation of the higher chloromethanes $CH_2Cl_2$, $CHCl_3$ and $CCl_4$, comprising parallel first and second chlorination reaction means A and B, means for reaction product combination and separation in downstream, discrete communicating relationship with each of said reaction means A and B, means for separating higher chloromethanes from combined reaction product, and means for recycling at least one separated higher chloromethane to said second reaction means B, said means for separation of the reaction product comprising a plurality of downstream means for separation of said combined reaction product, in serially communicating relationship, said first reaction means A including means for feeding methyl chloride thereto and said second reaction means B including means for feeding at least one higher chloromethane thereto, said separation means comprising a first separation unit for removing HCl from the reaction product, a second separation unit for removing $CH_3Cl$ from the reaction product, a third separation unit for removing $CH_2Cl_2$ from the reaction product and a fourth separation unit for removing $CHCl_3$ from the reaction product, the apparatus further comprising means for feeding unreacted $CH_3Cl$ removed by said second separation unit to said first separation unit for cooling of reaction product in said first separation unit.

12. Apparatus for the simultaneous preparation of the higher chloromethanes $CH_2Cl_2$, $CHCl_3$ and $CCl_4$, comprising parallel first and second chlorination reaction means A and B, means for reaction product combination and separation in downstream, discrete communicating relationship with each of said reaction means A and B, means for separating higher chloromethanes from combined reaction product, and means for recycling at least one separated higher chloromethane to said second reaction means B, said means for separation of the reaction product comprising a plurality of downstream means for separation of said combined reaction product, in serially communicating relationship, said first reaction means A including means for feeding methyl chloride thereto and said second reaction means B including means for feeding at least one higher chloromethane thereto, said separation means comprising a first separation unit for removing HCl from the reaction product, a second separation unit for removing $CH_3Cl$ from the reaction product, a third separation unit for removing $CH_2Cl_2$ from the reaction product and a fourth separation unit for removing $CHCl_3$ from the reaction product, the apparatus further comprising means for feeding $CH_2Cl_2$ removed by said third separation unit to feed to said second reaction means B.

13. Apparatus for the simultaneous preparation of the higher chloromethanes $CH_2Cl_2$, $CHCl_3$ and $CCl_4$, comprising parallel first and second chlorination reaction means A and B, means for reaction product combination and separation in downstream, discrete communicating relationship with each of said reaction means A and B, means for separating higher chloromethanes from combined reaction product, and means for recycling at least one separated higher chloromethane to said second reaction means B, said means for separation of the reaction product comprising a plurality of downstream means for separation of said combined reaction product, in serially communicating relationship, said first reaction means A including means for feeding methyl chloride thereto and said second reaction means B including means for feeding at least one higher chloromethane thereto, said separation means comprising a first separation unit for removing HCl from the reaction product, a second separation unit for removing $CH_3Cl$ from the reaction product, a third separation unit for removing $CH_2Cl_2$ from the reaction product and a fourth separation unit for removing $CHCl_3$ from the reaction product, the apparatus further comprising means for feeding $CHCl_3$ removed by said fourth separation unit to feed to said second reaction means B.

14. Apparatus for the simultaneous preparation of the higher chloromethanes $CH_2Cl_2$, $CHCl_3$ and $CCl_4$, comprising parallel first and second chlorination reaction means A and B, means for reaction product combination and separation in downstream, discrete communicating relationship with each of said reaction means A and B, means for separating higher chloromethanes from combined reaction product, and means for recycling at least one separated higher chloromethane to said second reaction means B, said means for separation of the reaction product comprising a plurality of downstream means for separation of said combined reaction product, in serially communicating relationship, said first reaction means A including means for feeding methyl chloride thereto and said second reaction means B including means for feeding at least one higher chloromethane thereto, said separation means comprising a first separation unit for removing HCl from the reaction product, a second separation unit for removing $CH_3Cl$ from the reaction product, a third separation unit for removing $CH_2Cl_2$ from the reaction product and a fourth separation unit for removing $CHCl_3$ from the reaction product, the apparatus further comprising gas scrubbing means located upstream of said means for reaction product combination, said scrubbing means being in parallel with means feeding effluent from said second reaction means B to said first separation unit.

15. The apparatus as defined by claim 14, further comprising means for feeding effluent from said second reaction means B to said gas scrubbing means.

16. The apparatus as defined by claim 14, further comprising means for feeding one or more higher chloromethanes exiting said gas scrubbing means to feed to said second reaction means B.

17. The apparatus as defined by claim 14, further comprising means for feeding at least one of $CH_2Cl_2$ and $CHCl_3$ exiting said third and fourth separation units to said gas scrubbing means.

18. The apparatus as defined by claim 14, further comprising means for feeding effluent from said second reaction means B to said gas scrubbing means and effluent from said gas scrubbing means to said first separation unit.

19. Apparatus for the simultaneous preparation of the higher chloromethanes $CH_2Cl_2$, $CHCl_3$ and $CCl_4$, comprising parallel first and second chlorination reaction means A and B, said first reaction means A including means for feeding $CH_3Cl$ thereto and said second reaction means B including means for feeding at least one of $CH_2Cl_2$ and $CHCl_3$ thereto; means for reaction product combination and separation in downstream, discrete communicating relationship with each of said reaction means A and B; means for separating higher chloromethanes from combined reaction product; means for recycling at least one separated higher chloromethane to said second reaction means B; said separating means including a first separation unit for removing HCl from the reaction product, a second separation unit for removing $CH_3Cl$ from the reaction product, a third separation unit for removing $CH_2Cl_2$ from the reaction product and a fourth separation unit for removing $CHCl_3$ from the reaction product; said second separation unit being located downstream of said first separation unit, said third separation unit being located downstream of said second separation unit and said fourth separation unit being located downstream of said third separation unit; means for feeding unreacted $CH_3Cl$ removed by said second separation unit to said feed to said first reaction means A; means for feeding $CH_2Cl_2$ removed by said third separation unit to said feed to said second reaction means B; and means for feeding $CHCl_3$ removed by said fourth separation unit to said feed to said second reaction means B.

20. The apparatus as defined by claim 19, further comprising means for scrubbing effluent from said second reaction means B located upstream of said means for reaction product combination, said scrubbing means including means for gas scrubbing feed to said second reaction means B.

21. The apparatus as defined by claim 19, further comprising means for feeding reaction product exiting said second separation unit to said feed to said second reaction means B, and means for feeding reaction product exiting said means B, and means for feeding reaction product exiting said third separation unit to said feed to said second reaction means B.

22. The apparatus as defined by claim 19, further comprising gas scrubbing means in parallel with means feeding effluent from said second reaction means B to said first separation unit; means for feeding effluent from said second reaction means B to said gas scrubbing means; means for feeding one or more higher chloromethanes exiting said gas scrubbing means to said feed to said second reaction means B; means for feeding at least one of $CH_2Cl_2$ and $CHCl_3$ exiting said third and fourth separation units to said gas scrubbing means; and means for feeding effluent from said gas scrubbing means to said first separation unit.

23. Apparatus for the simultaneous preparation of the higher chloromethanes $CH_2Cl_2$, $CHCl_3$ and $CCl_4$, comprising parallel first and second chlorination reaction means A and B, said first reaction means A including means for feeding $CH_3Cl$ thereto and said second reaction means B including means for feeding at least one of $CH_2Cl_2$ and $CHCl_3$ thereto; means for reaction product combination and separation in downstream, discrete communicating relationship with each of said reaction means A and B; means for separating higher chloromethanes from combined reaction product; means for recycling at least one separated higher chloromethane to said second reaction means B said separating means comprising a first separation unit for removing HCl from the reaction product, a second separation unit for removing $CH_3Cl$ from the reaction product, a third separation unit for removing $CH_2Cl_2$ from the reaction product and a fourth separation unit for removing $CHCl_3$ from the reaction product; said second separation unit being located downstream of said first separation unit, said third separation unit being located downstream of said second separation unit and said fourth separation unit being located downstream of said third separation unit; means for feeding unreacted $CH_3Cl$ removed by said second separation unit to said feed to said first reaction means A; means feeding effluent from said second reaction means B to said first separation unit; gas scrubbing means in parallel with said means feeding effluent from said second reaction means B to said first separation unit; means for feeding effluent from said second reaction means B to said gas scrubbing means; means for feeding one or more higher chloromethanes exiting said gas scrubbing means to said feed to said second reaction means B; means for feeding at least one of $CH_2Cl_2$ and $CHCl_3$ exiting said third and fourth separation units to said gas scrubbing means; and means for feeding effluent from said gas scrubbing means to said first separation unit.

* * * * *